(12) United States Patent
Lepore

(10) Patent No.: US 6,408,538 B1
(45) Date of Patent: Jun. 25, 2002

(54) METHOD OF STERILIZATION OF MUSICAL WIND INSTRUMENTS

(76) Inventor: Lorenzo Lepore, 117 Whitney Rd., Medford, MA (US) 02155

(*) Notice: Subject to any disclaimer, the term of this patent is extended or adjusted under 35 U.S.C. 154(b) by 0 days.

(21) Appl. No.: 09/953,340

(22) Filed: Sep. 14, 2001

Related U.S. Application Data (63) Continuation-in-part of application No. 09/635,342, filed on Aug. 9, 2000, now Pat. No. 6,345,449.
(60) Provisional application No. 60/147,887, filed on Aug. 9, 1999.

(51) Int. Cl.[7] .................................................. F26B 7/00
(52) U.S. Cl. .............................. 34/389; 34/380; 34/516
(58) Field of Search ........................... 34/380, 389, 390, 34/516, 92, 60; 206/14, 314; 422/4, 5, 28, 62, 105, 119

(56) References Cited

U.S. PATENT DOCUMENTS

| | | | |
|---|---|---|---|
| 3,476,506 A | 11/1969 | Andersen et al. | 21/91 |
| 4,107,976 A | 8/1978 | Andersen et al. | 73/52 |
| 4,145,186 A | 3/1979 | Andersen | 23/232 |
| 4,937,046 A | 6/1990 | Andersen et al. | 422/34 |
| 5,082,636 A | 1/1992 | Andersen | 422/294 |
| 5,118,471 A | 6/1992 | Andersen et al. | 422/34 |
| 5,135,715 A | 8/1992 | Andersen | 422/28 |
| 5,160,700 A | 11/1992 | Andersen et al. | 422/34 |
| 5,227,132 A | 7/1993 | Andersen et al. | 422/2 |
| 5,241,803 A | 9/1993 | Griffin | 53/425 |
| 5,302,358 A | 4/1994 | Andersen et al. | 422/305 |
| 5,816,395 A * | 10/1998 | Dougherty | 206/314 |

OTHER PUBLICATIONS

Zory Glaser, PhD–The Future of Ethylene Oxide as a Medical Device Sterilant in Healthcare Facilities—Infection Control Today—Apr. 1998.

David L. Lewis et al.—Cross–Contamination Potential with Dental Equipment—The Lancet—vol. 340; Nov. 21, 1992.

Elevating Standard of Infection Control—www.anpro.com Copyright ©1999 Andersen Products.

Andersen, L. et al.—An Introduction to Gas–Diffusion Sterilization (May 97) Devices & Diagnostic Industry,, pp. 137–150.

Mayworm, D.—100% EO Processing: Another Alternative (Aug. 96) Infection Control & Sterilization Technology, vol. 2, No. 8.

(List continued on next page.)

Primary Examiner—Denise L. Esquivel
Assistant Examiner—Mark Shulman
(74) Attorney, Agent, or Firm—Mintz, Levin, Cohn, Ferris, Glovsky and Popeo, P.C.

(57) ABSTRACT

A method of sterilizing musical instruments is provided. More particularly, a method of sterilizing musical wind instruments and accessories related thereto is provided for sterilizing, or at least sanitizing, musical wind instruments and accessories without damaging or degrading components of such instruments and accessories constructed of cloth, wood, plastic, rubber or fibrous materials. The method of the invention uses a gas diffusion process and a gas sterilant, such as ethylene oxide. A musical wind instrument and/or an accessory is placed in a gas diffusion bag and a sterilizing atmosphere is created within the gas diffusion bag by releasing ethylene oxide into the gas diffusion bag at a sufficient concentration to act as a sterilant. Ethylene oxide is heated to an appropriate temperature and maintained at such temperature for a sufficient time to achieve sterilization, or at least sanitization, of the musical wind instrument and/or accessory contained therein.

22 Claims, 6 Drawing Sheets

OTHER PUBLICATIONS

Andersen, Lintott, Hu.—Outsourcing Sterile Reprocessing (Jul. 97) Infection Control & Sterilization Technology, pp. 24–32.

Waldron, E.—Niche Players Can Thrive in the Global Market (Nov. 97) (Medical Device & Diagnostic Industry).

Sordellini, Paul J—Speeding EtO–Sterilized Products to Market with Parametric Release (Medical Device & Diagnostic Industry (Feb. 97).

Mayworm, Dan—Low Temperature Sterilization Revisited—Infection Control Sterilization Technology—Feb. 1998—p. 22.

Anprolene AN7D & E Sterilizers Brochure/Instruction Manual.

MD Industries Catalog Pages.

* cited by examiner

METHOD OF STERILIZATION OF MUSICAL WIND INSTRUMENTS

PRIOR PATENT APPLICATIONS

This application is a continuation-in-part application under 37 CFR §1.53(b) of U.S. nonprovisional patent application Ser. No. 09/635,342, filed Aug. 9, 2000 now U.S. Pat. No. 6,345,449, which claims priority to U.S. provisional patent application Serial No. 60/147,887, filed on Aug. 9, 1999, and is incorporated herein by reference.

FIELD OF THE INVENTION

The present invention provides a method of sterilizing musical wind instruments and their parts (e.g., mouthpieces), cases and/or accessories (collectively referred to herein as "accessories"). More particularly, the present invention provides a sterilization method using a gas diffusion process and a gas sterilant, such as ethylene oxide, to sterilize, or at least sanitize, musical wind instruments and/or their accessories.

BACKGROUND OF THE INVENTION

Playing musical instruments is a very popular activity in the United States and throughout the world. Musical instruments generally fall into three classes: string instruments, percussion instruments and wind instruments. The string instruments, i.e., violins, guitars, cellos and the like, produce musical tones by bowing or plucking strings which vibrate in audible frequencies. The percussion instruments, i.e., drums, gongs, cymbals, tympani and the like, produce sounds by providing a surface which is struck with a stick, mallet or similar object. One hybrid instrument, the piano, produces tones using strings which are struck by padded hammers that are controlled using a keyboard. Finally, the wind instruments produce musical tones when air is blown through them or across openings in them.

The wind instruments generally fall within two main categories. Brass instruments, such as trumpets, French horns, trombones, tubas and the like, are usually constructed of metals and include a bell shaped mouthpiece that the musician places against his or her lips. Woodwinds, such as clarinets, saxophones, oboes, bassoons and the like, are usually constructed of a variety of materials and include a single or double reed which is placed partially in the musician's mouth. One family of woodwinds, the flutes, do not include a reed, but rather have an aperture called an embouchure across which the musician blows to produce a musical tone.

A wide variety of materials are employed in constructing wind instruments. While the brass instruments are constructed primarily of metals, woodwinds tend to comprise a combination of woods, metals, plastics, rubbers and fibrous materials such as cotton. In fact, some flutes even use fish scales in the design of pads which cover and expose various keyholes. Since the wind instruments are played by blowing into them, it is natural that some of the musician's body fluids, including blood elements, saliva and water vapor, will accumulate in their interiors. Instruments that include curved portions often include a mechanism, called a spit-valve, that can be opened to allow accumulated fluids to be drained from the instrument.

Most serious musicians own their instruments and treat them as very personal objects. That notwithstanding, however, many beginning music students, particularly those in elementary and secondary schools, use instruments which they have borrowed from the institution in which they receive their musical training. Typically, a student may rent an instrument for a semester or a school year, returning it upon completion of the rental period. In many locations, the practice is to store the returned instrument until the next musician seeking such an instrument rents it. There is nothing to guarantee that each student will receive the same instrument from rental term to rental term.

As a result of these practices, student musicians often obtain instruments that have been rented and used by others. This raises health issues because at present little if anything is done to clean or sanitize instruments between users and/or rentals. Thus, while the exterior of the instruments may receive a polish, the interior remains coated with dried saliva and exhaled water vapor from the prior user. This raises potential problems since the interior of wind instruments, particularly when damp, can form an excellent environment for the growth of infectious microbes, such as bacteria or viruses, which can cause illness when ingested or inhaled. The medical model of universal precautions mandates that all patients and the devices used in their treatment (especially when bodily fluid contamination is included) be viewed as potentially infectious. Applying these precautions to musical wind instruments makes good sense, since musical wind instruments, and particularly their interiors, are repeatedly contacted with bodily fluids as a natural result of the musician playing the instrument.

Sterilization of instruments raises several difficult practical and technical problems. For example, on the practical side, any sterilization must be relatively affordable, simple and not overly time-consuming. On the technical side, the sterilization of items constructed of a variety of materials including organic materials such as woods and cotton is a challenge. Of course, any sterilization method employed must be one which causes virtually no physical damage to the instrument. This is an issue because many known sterilizing agents, such as ultraviolet radiation, are known to degrade organic materials such as wood.

Thus, a need exists for affordable and efficient methods which allow the sterilization, or at the very least, the sanitization, of musical wind instruments. These methods must also be such that they do not damage the musical wind instruments during the sterilization process.

SUMMARY OF THE INVENTION

The invention provides a method of sterilizing a musical wind instrument using a gas diffusion process. In a first embodiment of the invention, the method of sterilization comprises steps of placing one or more musical instruments and/or accessories in one or more open, sealable diffusion bags, evacuating air from the diffusion bag, sealing the diffusion bag to achieve a leak-proof seal, placing the diffusion bag in a chamber of a sterilizer or a temperature-controlled sterilization room equipped with an exhaust ventilation system, creating a sterilizing atmosphere within the diffusion bag by introducing a gas sterilant such as ethylene oxide or propylene oxide into the interior of the diffusion bag, heating the gas sterilant to an appropriate temperature, maintaining the temperature of the gas sterilant for a sufficient time to achieve sterilization, or at least sanitization, of the musical wind instrument, and removing the diffusion bag from the sterilization chamber or room with the musical wind instrument contained therein.

In a first aspect of the first embodiment, the sterilizing atmosphere is created within the interior of the gas diffusion bag by introducing a unit dose of ethylene oxide into the interior of the diffusion bag by a remotely-activated cartridge that releases 100% ethylene oxide gas into the diffusion bag upon activation by an external trigger. The unit dose of ethylene oxide is measured in relation to the volume of the interior of the gas diffusion bag. The ethylene oxide gas is heated to an appropriate sterilization temperature of about 45° C. to about 55° C., and maintained at such temperature for a sufficient time of about 4 to about 16 hours to achieve sterilization. After completion of sterilization, residual ethylene oxide gas molecules absorbed by gas-absorbent materials of the musical wind instrument and contained within the diffusion bag and the sterilization chamber are substantially removed by purging and exhausting ethylene oxide gas molecules for a sufficient time of about 16 to 24 hours to the outside atmosphere.

The gas diffusion bag is constructed of a suitable material that is tear-resistant and allows ethylene oxide to diffuse outwardly from the interior of the diffusion bag, such as, although not limited to, low density polyethylene.

In a second embodiment of the invention, the ethylene oxide gas is introduced into the interior of the gas diffusion bag to create the sterilizing atmosphere by a gas cylinder injector system. The gas cylinder injector system contains a gas cylinder containing 100% ethylene oxide and is equipped with an adjustably connected injector. The injector is inserted into the gas diffusion bag, withdraws or evacuates air from the diffusion bag, and injects ethylene oxide gas into the gas diffusion bag. The gas diffusion bag is then sealed to achieve a leak-proof seal. The injection of ethylene oxide into the gas diffusion bag proceeds within operation of a high-volume exhaust ventilation system that exhausts diffusing gas molecules to the outside atmospheres. The gas diffusion bag is thereafter placed either in the sterilization chamber of the sterilizer or into a temperature-controlled sterilization room. The gas cylinder injector system is conducive for use with multiple lots of individual gas diffusion bags.

The gas diffusion bag is constructed of a suitable material that is tear-resistant and allows ethylene oxide to diffuse outwardly from the interior of the diffusion bag, such as, although not limited to, low density polyethylene.

In a third embodiment of the invention, one or more musical wind instruments and/or accessories are contained in one or more musical instrument carrying cases and placed within the interior of one or more gas diffusion bags for sterilization which are subsequently placed into a sterilization chamber or room. During the sterilization process, ethylene oxide gas molecules diffuse through the instrument carrying cases and contact the musical wind instruments and/or accessories contained therein.

In a fourth embodiment of the invention, the sterilizing atmosphere is provided by a standard ethylene oxide sterilizer, such as an ethylene oxide sterilizer used by hospitals to sterilize medical instruments, or larger institutional sterilizers used by contract sterilization facilities. A gas diffusion bag containing one or more musical instruments and/or accessories is placed within a sterilization chamber of the ethylene oxide sterilizer and ethylene oxide is released into the sterilization chamber. Upon heating ethylene oxide to an appropriate temperature, ethylene oxide gas molecules diffuse through the diffusion bag. Ethylene oxide gas molecules circulate throughout the diffusion bag, contacting the musical wind instruments and/or accessories contained therein. The diffusion bag is constructed of a tear-resistant material that is in part permeable to ethylene oxide in order to facilitate diffusion of ethylene oxide from the atmosphere of the sterilization chamber into the interior of the diffusion bag. In one embodiment, the diffusion bag is constructed of high density polyethylene. The diffusion bag further includes a band of material in part highly permeable to ethylene oxide, such as, although not limited to, the material commercially-known as TYVEK® and available from E. I. duPont de Nemours and Co. The band of TYVEK® is incorporated with and surrounds at least a portion of the perimeter of the diffusion bag. The diffusion bag is sealed by a suitable method to form a substantially leak-proof and tamper-proof seal. In addition, the method of this embodiment further includes degassing the diffusion bag for a predetermined period of time to reduce ethylene oxide to a safe level for use.

In a fifth embodiment of the method of the invention, the method provides for sterilization of large or multiple lots of musical instruments and/or accessories and comprises placing one or more musical instruments and/or accessories into the interior of one or more containers; evacuating air from the container; sealing the container; positioning the container in a sterilization room having temperature control and a ventilation system for removal of exhaust gas from the sterilization room; creating a sterilizing atmosphere within the interior of the container by releasing into the sterilization room ethylene oxide at a concentration sufficient to act as a sterilant; heating ethylene oxide to an appropriate sterilization temperature; maintaining the sterilization temperature of the ethylene oxide for a sufficient time to sterilize the musical instrument and/or accessories; purging the container for a set purge cycle time to remove residual ethylene oxide; removing the container from the chamber after the expiration of the sterilization and purging; confirming by use of one or more biological and/or chemical sterilization monitoring devices that one or more sterilization parameters have been met; degassing the container to reduce ethylene oxide to a level safe for end-users; and storing and supplying the musical instruments and/or accessories in the container for end-use.

In a first aspect of the fifth embodiment of the method of the invention, the container includes a diffusion bag constructed of a tear-resistant material that is in part permeable to ethylene oxide in order to facilitate diffusion of ethylene oxide from the atmosphere of the sterilization room into the interior of the diffusion bag. In one embodiment, the diffusion bag is constructed of high density polyethylene. The diffusion bag further includes a band of in part highly permeable material like TYVEK®, which is incorporated with and surrounds at least a portion of the perimeter of the diffusion bag. The diffusion bag is sealed by a suitable method to form a substantially leak-proof and tamper-proof seal.

BRIEF DESCRIPTION OF THE DRAWINGS

For a better understanding of the invention, reference is made to the drawings which are incorporated herein by reference and in which.

DETAILED DESCRIPTION OF THE INVENTION

Illustrative embodiments of the invention described below provide a method of sterilizing musical wind instruments and/or accessories by a gas diffusion process using a gas sterilant. Those skilled in the art will appreciate, however, that embodiments in accordance with the invention are not limited to sterilizing musical wind instruments, but also may be used to sterilize other types of musical instruments, including string musical instruments.

Embodiments of the invention will be described below with reference to FIGS. 1–6 which are presented herein for the purpose of illustrating embodiments and are not intended to limit the scope of the invention. The terms sterile, sterilize, sterilized, sterilizing, sterilizer and sterilization as used herein refer to processes, conditions, states or equipment for achieving at least the sanitization of musical instruments and/or accessories. By sanitization is meant at least a reduction of infectious microbes or other elements on musical instruments and/or accessories to a level that is incapable of causing infection, causing illness or endangering health. Preferably, treatment as described herein will render the instruments and/or accessories completely free from infectious microbes or other elements Referring to FIG. 1, a first embodiment of the invention provides a method of sterilizing one or more musical wind instruments and/or accessories by a gas diffusion process including steps of placing one or more musical instruments and/or accessories in a gas diffusion bag in step 110; providing a source of a gas sterilant, such as, although not limited to, ethylene oxide or propylene oxide, in step 120; evacuating air from the gas diffusion bag in step 125; sealing the gas diffusion bag in step 130 to form a substantially leak-proof seal; placing the gas diffusion bag in a chamber of a sterilizer or a temperature-controlled sterilization room equipped with an exhaust ventilation system in step 140; creating a sterilizing atmosphere in the gas diffusion bag by introducing the gas sterilant into the gas diffusion bag in step 150; and heating the gas sterilant to a sterilization temperature in step 160.

Figure 2:
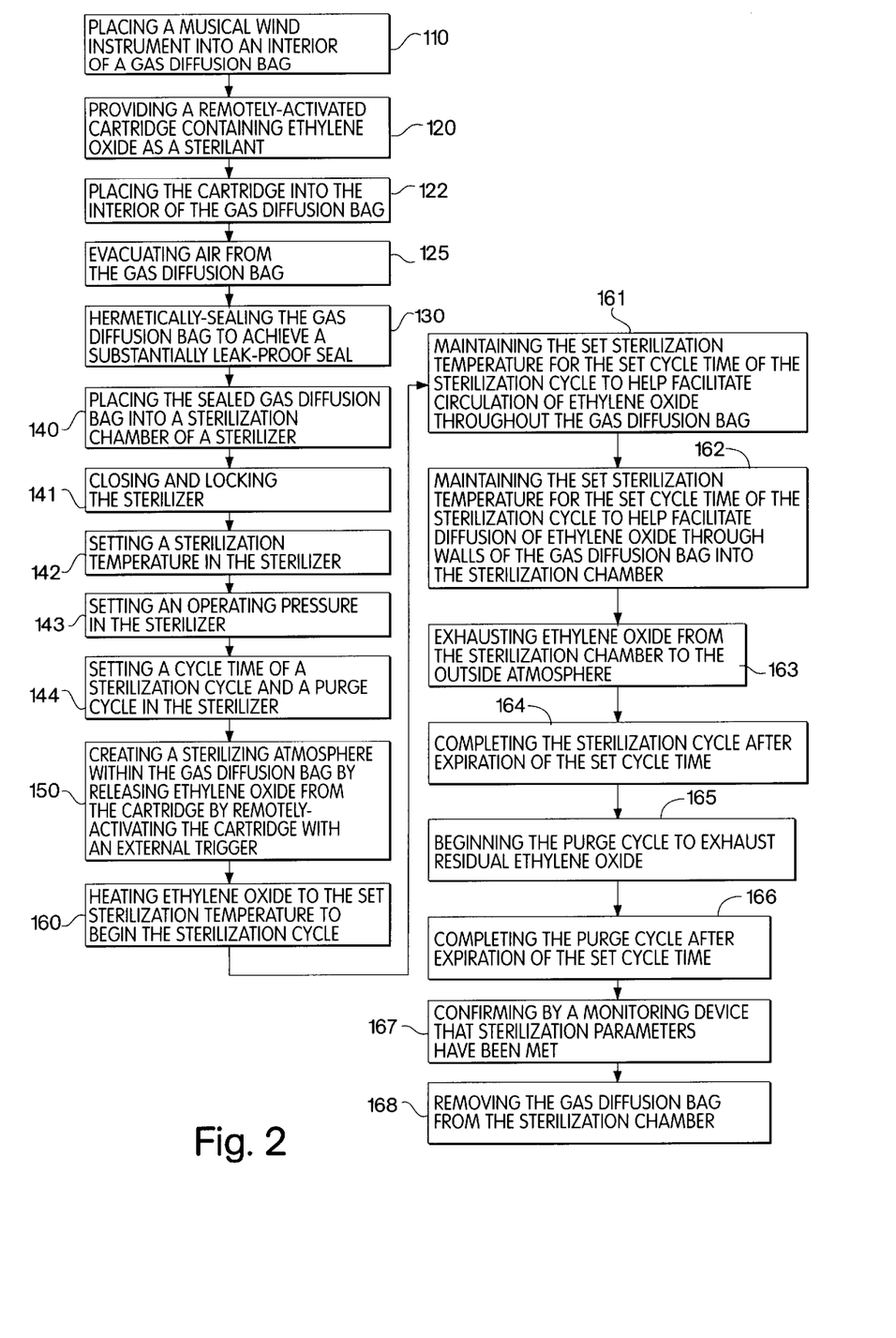
FIG. 2 is a flow diagram illustrating another version of the first embodiment.

Referring to FIG. 2, in a first aspect of the first embodiment, the method employs ethylene oxide as the gas sterilant and includes in step 110 placing one or more musical wind instruments and/or accessories into an interior of the gas diffusion bag, which is sized to accommodate one or more musical instruments and/or accessories and to provide sufficient interior volume for adequate circulation of ethylene oxide throughout the diffusion bag.

A source of ethylene oxide is provided in step 120 and includes a remotely-activated cartridge, which contains a measured unit dose of about 100% ethylene oxide. The quantity of the measured unit dose of ethylene oxide is calculated in relation to the size or volume of the gas diffusion bag, rather than the volume of a sterilization chamber of a sterilizer or sterilization room. Measuring unit doses of ethylene oxide according to the size or volume of the gas diffusion bag helps facilitate economy in the use of ethylene oxide as a sterilant by avoiding waste, while ensuring that the parameters of sterilization are met. In addition, the flexibility of the gas diffusion process used in the method of the invention allows use of ethylene oxide to be based upon the actual musical wind instrument and/or accessories to be sterilized rather than the volume of the sterilization chamber.

The cartridge is placed directly into the interior of the gas diffusion bag in step 122 together with the musical wind instruments and/or accessories to be sterilized. Air is evacuated from the gas diffusion bag in step 125. The gas diffusion bag is thereafter hermetically sealed, or sealed by other comparable methods well known in the art, in step 130 to achieve a substantially leak-proof seal. The sealed gas diffusion bag is subsequently placed in a sterilization chamber of the sterilizer or sterilization room in step 140. A door of the sterilizer is closed and locked in step 141.

In step 142, the sterilization temperature is set in the sterilizer or room. In addition, in step 143, a pressure under which the sterilizer or room operates is set, and, in step 144, cycle times of a sterilization cycle and a purge cycle are set in the sterilizer or room. Sterilization temperature is about 45° C. to about 55° C., and preferably about 50° C. The sterilization cycle operates for about 4 hours to about 16 hours at a pressure of about 0 to about 1 inch vac. The purge cycle operates for about 12 hours to about 24 hours. The cycle times of the sterilization cycle and the purge cycle depend upon the type of musical instruments and/or accessories to be sterilized and the materials with which the musical instruments and/or accessories are constructed. For example, musical instruments and/or accessories with highly detailed structures and intricate designs would require relatively longer sterilization cycles than musical instruments and/or accessories of simpler structures and designs in order to ensure a sufficient amount of the gas sterilant circulates or penetrates into the musical instruments and/or accessories and contacts substantially all surfaces of the musical instruments and/or accessories. In addition, various materials used to construct components of musical instruments and accessories, such as cloth, woods, plastics, rubbers and fibrous materials, are gas absorbent materials that require relatively shorter or longer purge cycles for the gas sterilant absorbed by such materials to be substantially diffused or purged from the materials after the sterilization cycle is complete.

In step 150, ethylene oxide is subsequently introduced into the gas diffusion bag to create the sterilizing atmosphere. The cartridge is remotely activated and opened to release ethylene oxide into the gas diffusion bag by pressing a trigger located exterior to the sterilizer. Ethylene oxide gas is heated to the set sterilization temperature in step 160 to begin the sterilization cycle. As ethylene oxide is released from the cartridge, ethylene oxide gas molecules permeate throughout the gas diffusion bag. Kinetic energy of the heated ethylene oxide gas causes the gas molecules to spread out by their own velocity into substantially every cubic centimeter of the interior volume of the gas diffusion bag. Ethylene oxide circulates around and penetrates into the musical wind instruments and/or accessories contained within the gas diffusion bag. Ethylene oxide kills microbes on substantially all surfaces of the musical wind instruments and/or accessories that are contacted by circulating ethylene oxide gas molecules without damaging or degrading components of the musical wind instrument, particularly components constructed of cloth, wood, cloth, plastic or rubber. The elevated sterilization temperature maintained throughout the set cycle time of the sterilization cycle, as described below in steps 161 and 162, maintains the kinetic energy of the ethylene oxide gas, which helps to facilitate the circulating and penetrating action of the ethylene oxide gas molecules in the gas diffusion bag.

As the concentration of ethylene oxide gas molecules increases inside the gas diffusion bag by release of gas molecules from the cartridge, ethylene oxide gas molecules circulate throughout the gas diffusion bag and gradually diffuse through walls of the bag into the sterilization chamber or room, as long as the set sterilization temperature is maintained in steps 161 and 162. The ethylene oxide gas molecules which are diffused into the sterilization chamber or room are exhausted to the outside atmosphere by an exhaust ventilation system of the sterilizer in step 163. More ethylene oxide gas molecules are released into the gas diffusion bag from the cartridge than are diffused from the gas diffusion bag into the sterilization chamber or room during initial hours of the sterilization cycle. Eventually, during the course of the sterilization cycle, the release of gas molecules and diffusion of gas molecules from the gas diffusion bag are about equal. Ethylene oxide is finally depleted from the cartridge to exhaust the source of the ethylene oxide. Ethylene oxide gas molecules continue to diffuse into the sterilization chamber or room for the remainder of the sterilization cycle.

The sterilization cycle is complete after the expiration of the set cycle time of at least about 4 hours in step 164. The amount of residual ethylene oxide gas molecules inside the gas diffusion bag and the sterilization chamber or room is small. The purge cycle begins in step 165 for the set cycle time of at least about 16 hours to remove and exhaust all remaining ethylene oxide gas molecules from the musical wind instrument, the gas diffusion bag and the sterilization chamber or room to the outside atmosphere prior to opening the sterilizer. The purge cycle is complete at the expiration of the set cycle time in step 166.

After completion of the purge cycle, the gas diffusion bag containing the musical instruments and/or accessories is removed from the sterilization chamber or sterilization room in step 167. Sterilization monitoring devices or systems, such as biological and/or chemical indicators well known to those skilled in the art are used in step 168 to confirm that the sterilization parameters have been met.

The gas diffusion bag is thereafter used to store and transport the musical instruments and accessories in a sterilized state, thereby maintaining sterility of the instruments and accessories until such time as end-users wish to remove the instrument from the gas diffusion bag for use. In one embodiment, the gas diffusion bag includes a color chemical sterilization indicator incorporated therein. The color chemical sterilization indicator confirms by a color change that the gas diffusion bag has been exposed to the ethylene oxide sterilization process, and demonstrates to the end-users that the contents of the gas diffusion bag are sterile or at least sanitized. In addition, providing sterilized musical instruments and accessories to end-users in the gas diffusion bag demonstrates that sterility of the instruments and accessories contained therein have been maintained during storage and distribution.

Both new and used musical instruments and accessories may be similarly sterilized by the method of the invention. New musical wind instruments and accessories, upon completion of manufacture, may be factory-sterilized by the method of the invention prior to shipment to distributors, retail outlets and other end-users. In addition, used musical wind instruments and accessories may be sterilized by the method of the invention prior to transfer of musical wind instruments and accessories from previous end-users to new end-users. The sterilization method of the invention substantially reduces the potential of exposure of new end-users to infectious microbes, such as bacteria and viruses, residing in musical wind instruments and accessories that cause illness when ingested or inhaled. In addition, the method of the invention substantially reduces the possibility of spreading infectious microbes among the numerous users of used musical wind instruments and accessories during their useful lifetime.

The gas diffusion bag is constructed of a suitable material that is tear-resistant and porous to ethylene oxide gas, such as, although not limited to, low density polyethylene. For example, polyethylene gas diffusion bags available from Andersen Products, Inc. of Haw River, N.C., are suitable diffusion bags for sterilization of musical wind instruments according to the method of the invention. Although such gas diffusion bags are tear-resistant, should a leak in the diffusion bag result, the leak is not critical to the method of the invention due to the negative air pressure that is established within the sterilizer or room during the sterilization and purge cycles. The negative air pressure in the sterilization chamber or room draws off ethylene oxide gas molecules and exhausts the gas molecules through the sterilizer or room ventilation system. The sterilizer or room, in effect, acts as an exhaust hood to evacuate diffusing ethylene oxide gas molecules, thereby promoting safety in the use of ethylene oxide as a gas sterilant.

In addition, the sterilizer or room and ethylene oxide cartridges described above, as well as other related equipment required to execute the sterilization method of the invention, are commercially available from a number of sources, including Andersen Products, Inc. of Haw River, N.C.

Figure 3:
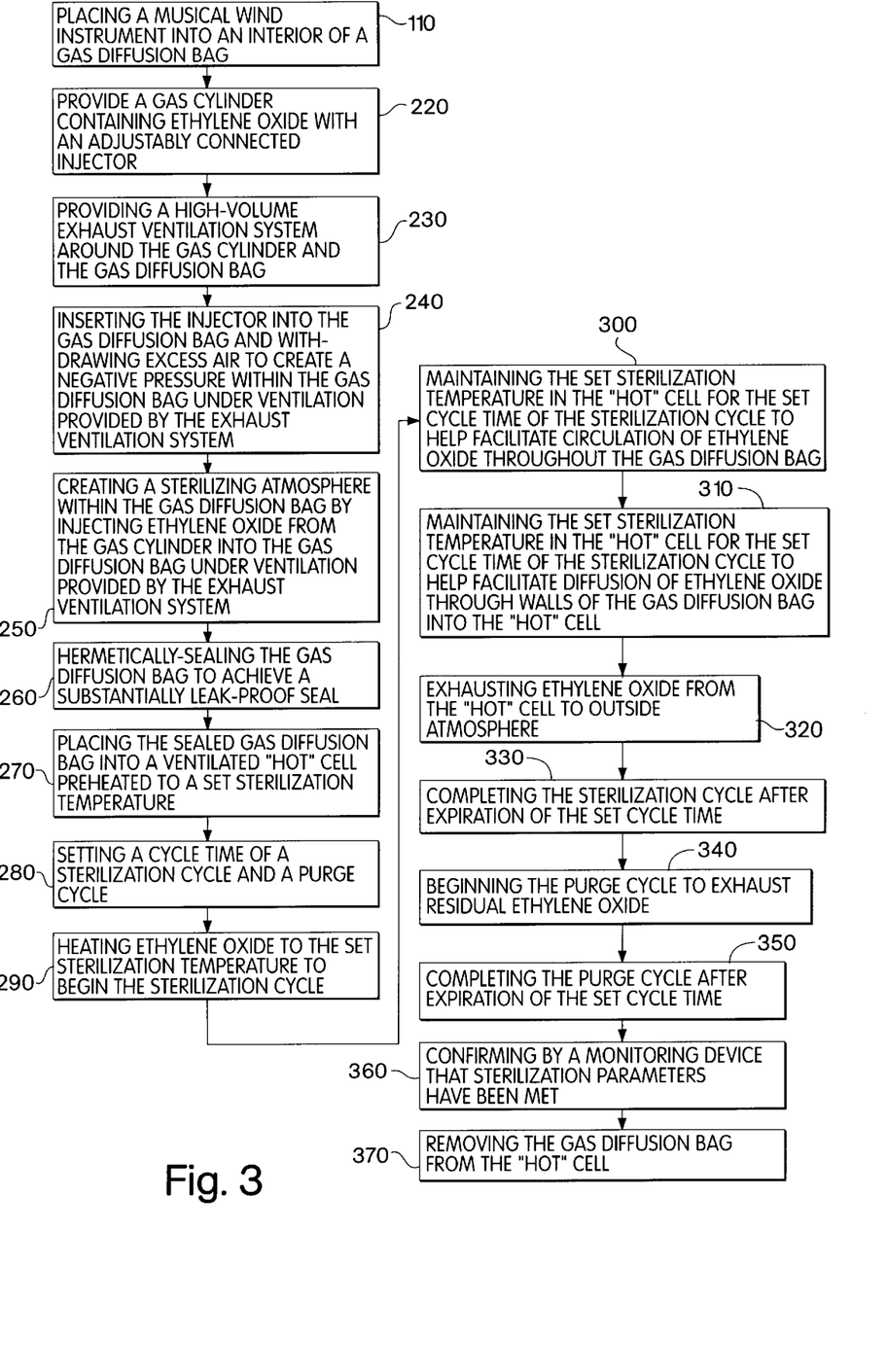
FIG. 3 is a flow diagram illustrating a second embodiment of the method of the invention.

Referring to FIG. 3, a second embodiment of the method of the invention includes creating the sterilizing atmosphere within the gas diffusion bag by introducing ethylene oxide into the gas diffusion bag with a gas cylinder injector system. The gas cylinder injector system injects a measured unit dose of ethylene oxide from a gas cylinder into the gas diffusion bag. The gas cylinder injector system is provided in step 220 and includes a gas cylinder with an injector adjustably connected to the gas cylinder for injecting ethylene oxide gas into individual diffusion bags. In step 230, a high-volume exhaust ventilation system is provided around the gas cylinder injector system and the gas diffusion bag to protect an operator of the gas cylinder injector from diffusing ethylene oxide gas during injection of ethylene oxide into the gas diffusion bag. The injector is inserted into the gas diffusion bag and withdraws excess air from the gas diffusion bag in step 240, under ventilation provided by the exhaust ventilation system, thereby creating a negative pressure within the gas diffusion bag. The injector subsequently injects a measured unit dose of ethylene oxide from the gas cylinder into the gas diffusion bag in step 250, creating a sterilizing atmosphere within the gas diffusion bag. Thereafter, in step 260, the gas diffusion bag is sealed, either hermetically or by other methods well known in the art, to achieve a substantially leak-proof seal. The gas diffusion bag is then placed in a "hot" cell in step 270, such as a preheated, ventilated chamber or room, in which the sterilization temperature is maintained and the sterilization cycle proceeds. Rather than relying upon individual cartridges of ethylene oxide inserted into each gas diffusion bag, the use of the gas cylinder injector system provides efficiency in sterilizing multiple lots of musical wind instruments and/or accessories during the sterilization cycle. In addition, the use of the high-volume exhaust ventilation system and the negative pressure created within the gas diffusion bag serve to ensure that the operator is not exposed to diffusing gas.

Figure 1:
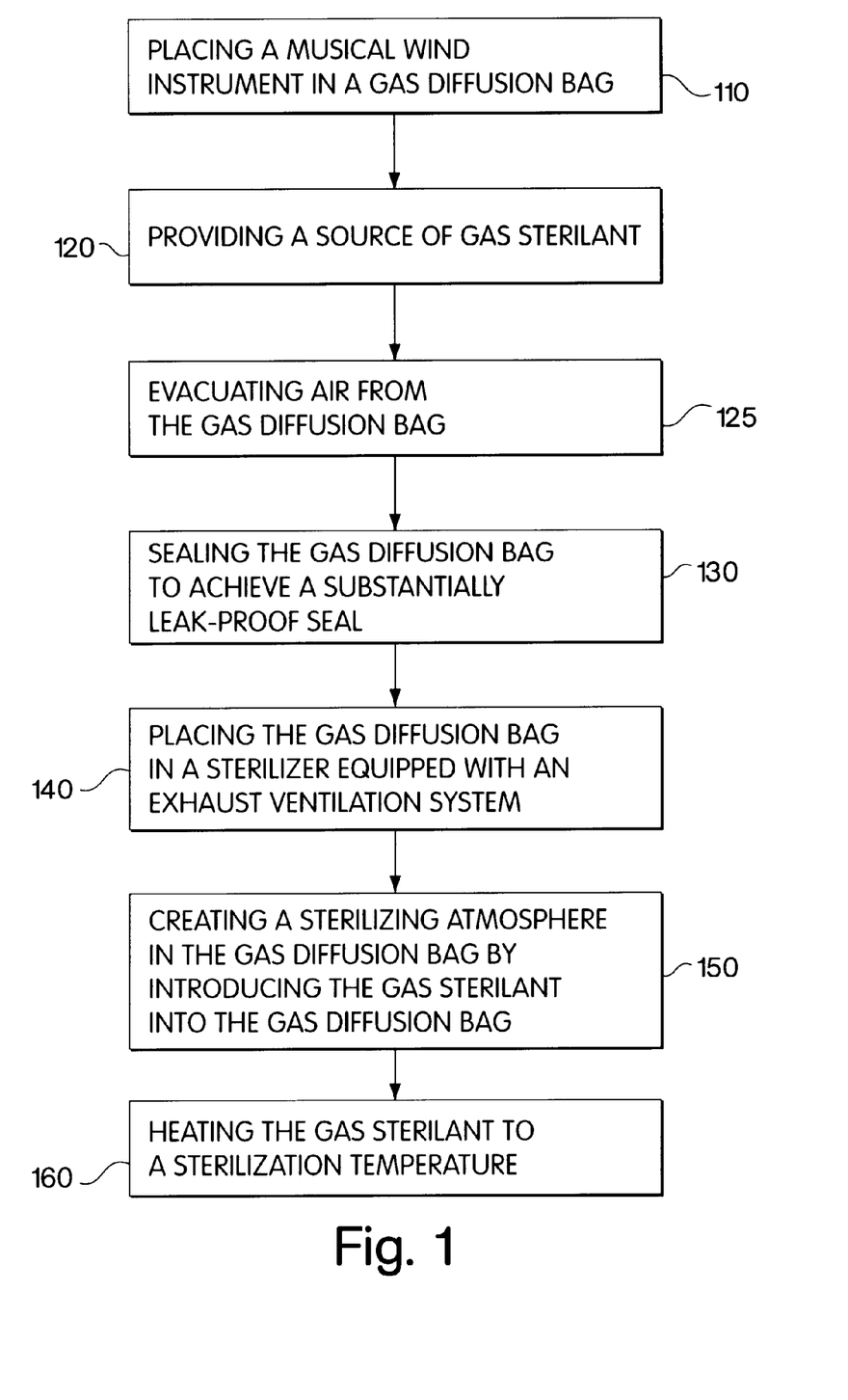
FIG. 1 is a flow diagram illustrating a first embodiment of a method of the invention.

The sterilization of the musical wind instruments and/or accessories thereafter proceeds similarly to the first embodiment as illustrated in FIGS. 1 and 2, including the steps of setting the cycle times of the sterilization and purge cycles in step 280; heating the ethylene oxide gas contained in the gas diffusion bag to the sterilization temperature in step 290; maintaining the sterilization temperature to help facilitate circulation of ethylene oxide gas molecules throughout the gas diffusion bag and into the musical wind instruments and/or accessories contained therein in step 300; maintaining the sterilization temperature in step 310 to help facilitate diffusion of ethylene oxide gas molecules through walls of the gas diffusion bag and into the "hot" cell; exhausting ethylene oxide gas molecules that permeate through walls of the gas diffusion bag into the "hot" cell to the outside atmosphere in step 320; completing the sterilization cycle after the set cycle time in step 330; beginning the purge cycle in step 340 to exhaust residual ethylene oxide; completing the purge cycle after expiration of the set cycle time in step 350; confirming by a monitoring device or system that the sterilization parameters have been met in step 360; and, finally, removing the gas diffusion bag from the "hot" cell in step 370.

Figure 4:
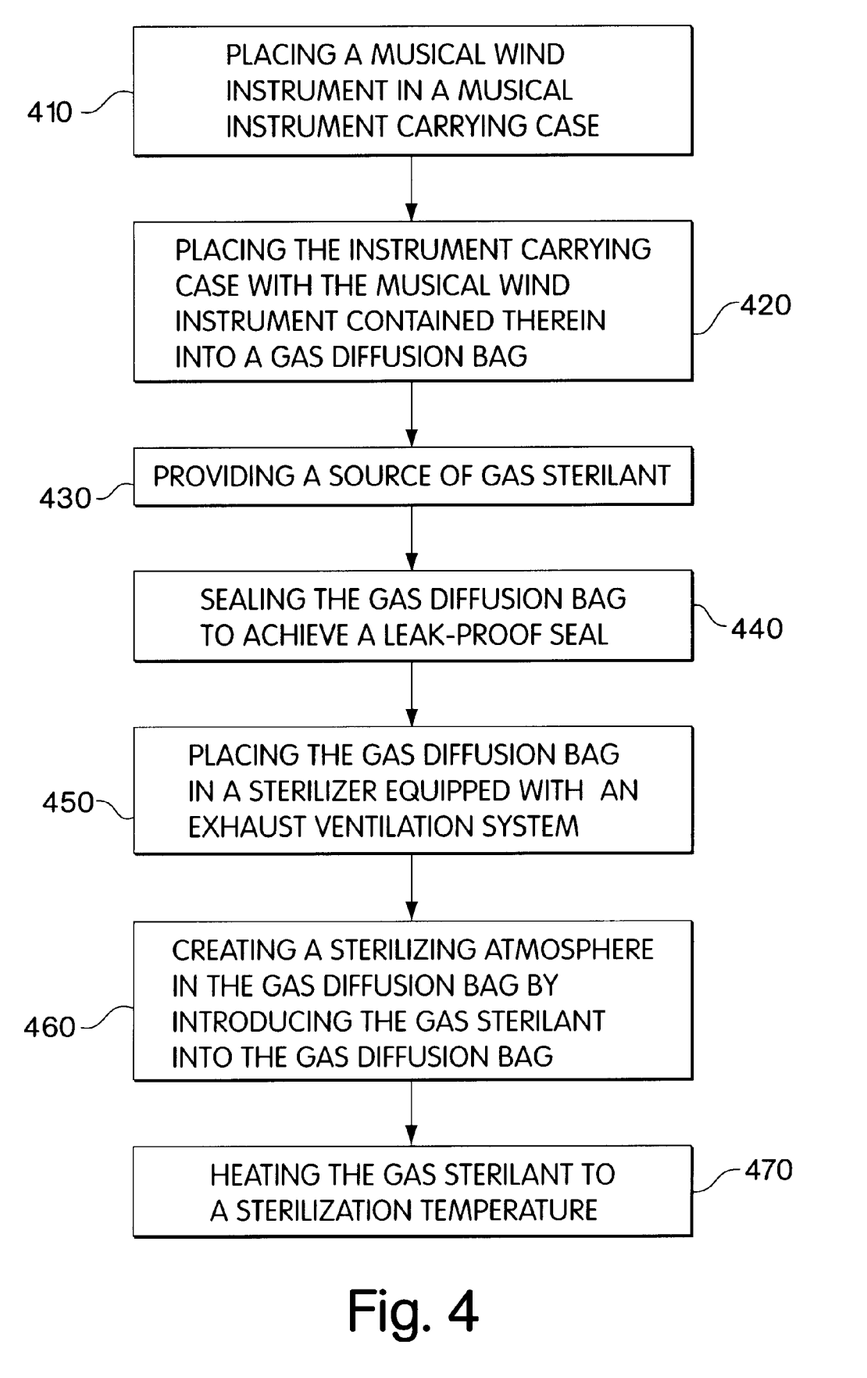
FIG. 4 is a flow diagram illustrating a third embodiment of the method of the invention.

Referring to FIG. 4, a third embodiment of the method of the invention includes sterilizing one or more musical wind instruments and/or accessories while instruments and/or accessories are contained in instrument carrying cases in step 410. The carrying cases containing the musical wind instruments and/or accessories are placed directly into one or more gas diffusion bags in step 420. A source of a gas sterilant is provided in step 430, such as, although not limited to, the cartridge of the first embodiment or the gas cylinder injector system of the second embodiment. The gas diffusion bags are similarly sealed as described above according to well known methods to form a substantially leak-proof seal in step 440. Thereafter, the method of sterilization of the musical wind instruments and/or accessories contained in the instrument carrying cases proceeds as described above in the first embodiment illustrated in FIG. 1, including the steps of placing the gas diffusion bags in a sterilizer or room equipped with an exhaust ventilation system in step 450; creating a sterilizing atmosphere within the gas diffusion bags by introducing the gas sterilant into the gas diffusion bag in step 460; and heating the sterilant to a set sterilization temperature in step 470. Ethylene oxide gas is capable of diffusing through walls of the instrument carrying cases to circulate around and penetrate into the musical wind instrument and/or accessories contained therein, thereby killing microbes on substantially all surfaces of the musical wind instruments and/or accessories which are contacted by circulating ethylene oxide gas molecules. An advantage of this embodiment includes providing the carrying case in a sterilized state as well as the musical wind instruments and/or accessories to further reduce the possibility of spread of infectious microbes between end-users of the musical wind instruments.

Figure 5:
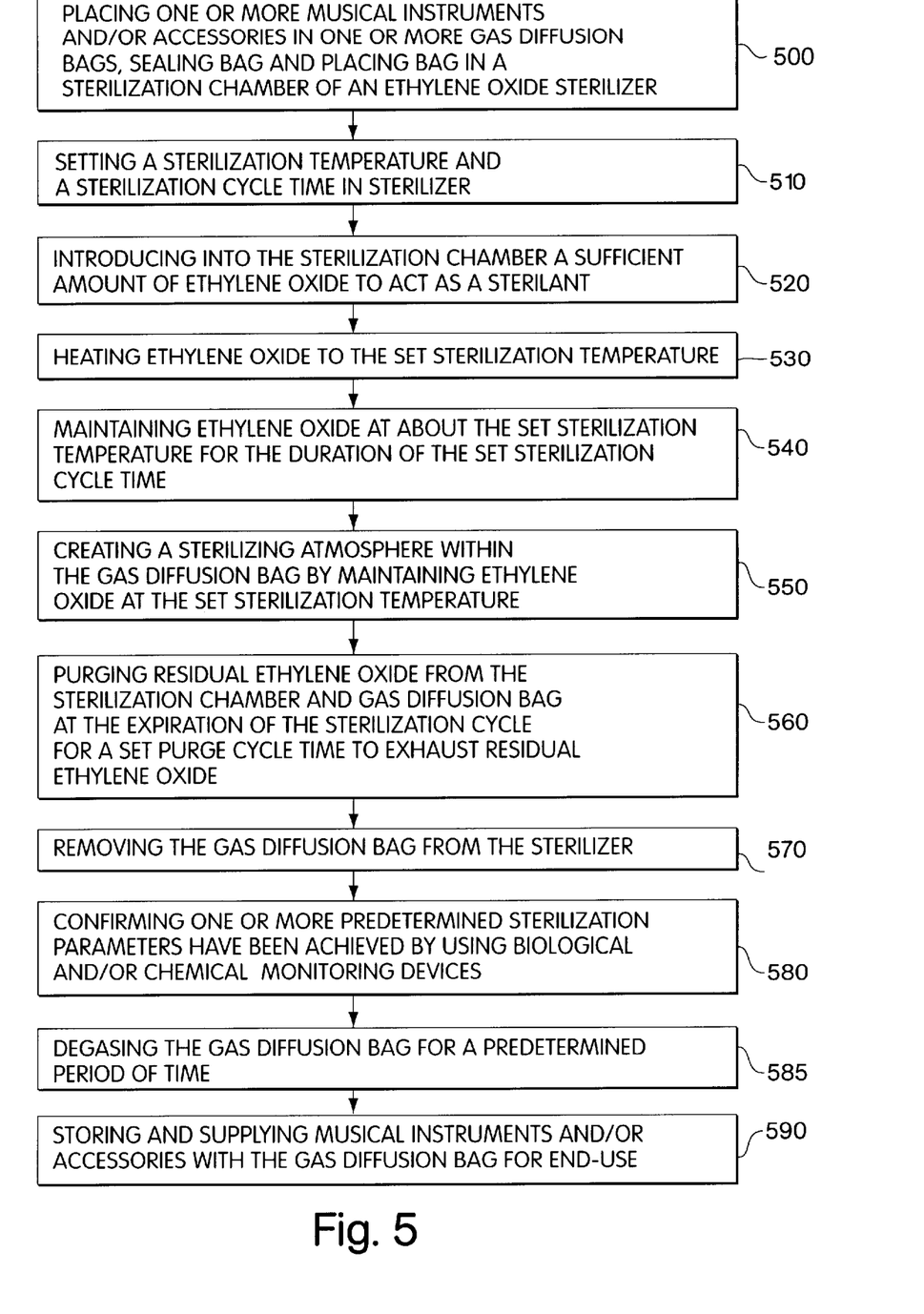
FIG. 5 is a flow diagram illustrating a fourth embodiment of the method of the invention.
Figure 6:
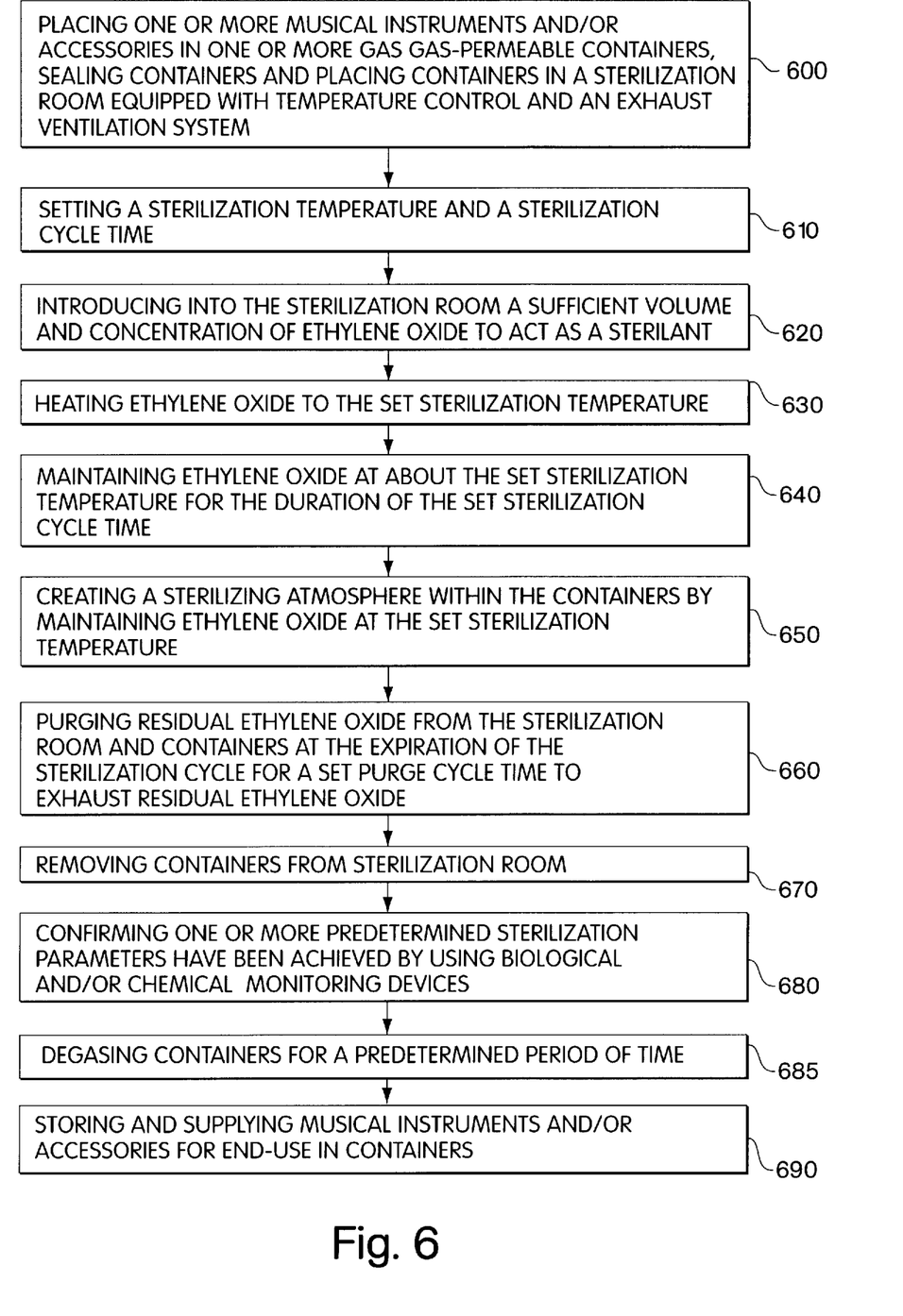
FIG. 6 is a flow diagram illustrating a fifth embodiment of the method of the invention.

Referring to FIG. 5, a fourth embodiment of the method according to the invention provides sterilization of one or more musical wind instruments and/or accessories using standard ethylene oxide sterilizers similar to the type of sterilizers used by hospitals and laboratories for sterilization of medical instruments. For instance, AMSCO® ethylene oxide sterilizers available from Steris Corporation of Mentor, Ohio may be used to sterilize musical wind instruments and/or accessories. In addition, large institutional sterilizers used by contract sterilization facilities may be used to practice the method of sterilizing musical instruments and/or accessories according to the invention. In this embodiment, one or more musical wind instruments and/or accessories are placed within one or more gas diffusion bags constructed of high density polyethylene. The gas diffusion bags are sealed and then placed within a sterilization chamber of the ethylene oxide sterilizer in step 500. A sterilization temperature and a sterilization cycle time are set in the ethylene oxide sterilizer in step 510. A sufficient amount of ethylene oxide to act as a sterilant such as 100% ethylene oxide gas is introduced into the sterilization chamber in step 520 to create a sterilizing atmosphere within the gas diffusion bag. Ethylene oxide is heated to the set sterilization temperature in step 530, and thereafter maintained for the set sterilization cycle time in step 540. During the sterilization cycle, ethylene oxide gas molecules diffuse through the wall of a gas diffusion bag, permitting entry of ethylene oxide gas molecules into the interior of the gas diffusion bag. Ethylene oxide molecules circulate and penetrate the musical wind instruments and/or accessories contained within the gas diffusion bag, contacting substantially all surfaces of the musical wind instruments and/or accessories to achieve a sterilized condition. By maintaining the sterilization temperature for the duration of the sterilization cycle time in step 550, a sterilizing atmosphere is created within the interior of the gas diffusion bag.

Upon expiration of the sterilization cycle, the method includes a purge cycle for a set cycle time to exhaust residual ethylene oxide from the sterilization chamber and gas diffusion bag in step 560. The method further includes confirming after the expiration of the sterilization and purge cycles that one or more predetermined sterilization parameters have been achieved. In step 570, the gas diffusion bag is removed from the sterilization chamber of the ethylene oxide sterlizer, and in step 580 confirmation of whether one or more sterilization parameters has been met is conducted by employing one or more biological and/or chemical sterilization monitoring devices. For instance, in one embodiment, an ethylene oxide biological indicator such as the biological indicators available from SPS Medical Supply Corp. of Rush, N.Y. is placed within the sterilization chamber and/or positioned proximate to the gas diffusion bag to detect and indicate whether the most resistant microbes, typically spores, have been killed. The musical instruments and/or accessories are then subject to a degassing phase for a predetermined period of time in step 585 to reduce ethylene oxide in the gas diffusion bag and the musical instruments and/or accessories contained therein to a level safe for end-users. The musical instruments and/or accessories are thereafter stored and supplied in the gas diffusion bag for end-use in step 590.

The gas diffusion bag employed in the fourth embodiment of the method of the invention is constructed of a suitable material in part permeable to ethylene oxide, such as, although not limited to, 3 mil high density polyethylene. High density polyethylene permits diffusion of ethylene oxide through the wall of the gas diffusion bag and into the interior of the gas diffusion bag to create a sterilizing atmosphere therein. In addition, one or more bands, strips or panels of a suitable material in part highly permeable to ethylene oxide is incorporated with the gas diffusion bag. For instance, in this embodiment, a band of the highly permeable material commercially known as TYVEK® and available from E. I. duPont de Nemours and Co. is incorporated with and encompasses or surrounds at least a portion of the perimeter of the gas diffusion bag. The TYVEK® band is sized to facilitate diffusion of a sufficient amount of ethylene oxide into the interior of the gas diffusion bag in order to increase the level of ethylene oxide inside the gas diffusion bag and reduce the time required for sterilization, while maintaining an economy with respect to the costs to manufacture the gas diffusion bag. In the present embodiment, the TYVEK® band is preferably about 4 inches wide and located around the base of the gas diffusion bag.

The TYVEK® band gas diffusion bag as described above is available from KNF Flexpak Corp. of Ronkonkoma, N.Y., and comprises suitable overall dimensions to accommodate musical instruments and/or accessories of various sizes and shapes. The gas diffusion bag is preferably sized to provide sufficient interior volume within the bag to allow ethylene oxide to readily circulate throughout the bag interior and contact the surfaces of the musical instruments and/or accessories contained therein. In addition, the gas diffusion bag is preferably sized to accommodate musical instruments and/or accessories contained within instrument cases in order to simultaneously sterilize both musical instruments and/or accessories and instrument cases. The preferred sizes of the gas diffusion bag include, although are not limited to, 4×2 inches, for containing mouth pieces and small accessories, 16×29 inches, 33×46 inches and 28×52 inches.

Prior to sterilization, the gas diffusion bag is sealed by any method well known in the art that produces a substantially leak-proof and tamper-proof seal. The desired seal is impermeable to gas sterilant and cannot be easily manually opened. In this embodiment, the gas diffusion bag is preferably opened by cutting the seal or the bag after sterilization. In addition, the gas diffusion bag is sealed with a suitable adhesive to form a substantially gas-impermeable, leakproof and tamper-proof seal.

As described above, the method includes using one or more biological and/or chemical monitoring devices to confirm that one or more set sterilization parameters have been achieved during the sterilization cycle. In this embodiment, the gas diffusion bag further includes one or more chemical monitoring devices incorporated with or affixed to the gas diffusion bag to indicate that a desired level of sterilization is achieved. Such a chemical monitoring device includes chemical color sterilization indicators such as those available from Etigam of The Netherlands. Upon completion of the sterilization cycle, the chemical color sterilization indicator confirms by a color change that the gas diffusion bag has been subjected to the ethylene oxide sterilization process, and demonstrates that the contents of the gas diffusion bag are sterile or at least sanitized. The chemical color indicator changes from one color to another upon exposure to ethylene oxide for a predetermined period of time. Providing sterilized musical instruments and accessories to end-users in the gas diffusion bag with a color sterilization indicator demonstrates the sterility and safety of the instruments and accessories contained therein. In .addition, the color sterilization indicator helps to promote confidence in end-users that the musical instruments and/or accessories contained in the gas diffusion bag have met a particular set of standards with respect safety and health and that such standards have been maintained during shipping and storing of the musical instruments and/or accessories.

Referring to FIG. 5, a fifth embodiment of the method of the invention provides sterilization of one or more musical instruments and/or accessories using a sterilization room equipped with temperature control and an exhaust ventilation system in which a gas sterilant is provided to sterilize musical instruments and/or accessories contained therein. The method provides efficiency in sterilizing large or multiple lots of musical instruments and/or accessories. The method includes placing one or more musical instruments and/or accessories in one or more containers, sealing the containers and then placing the containers within the sterilization room in step 600. Containers are constructed of a suitable material sufficiently permeable to a gas sterilant such that the gas sterilant diffuses from the atmosphere of the sterilization room through a container wall into the interior of the container during a sterilization cycle, thereby sterilizing the musical instruments and/or accessories contained therein. Containers are sealed by any method well known in the art to produce a substantially gas-impermeable, leak-proof and tamper-proof seal. Once the containers are placed within the sterilization room, the method includes setting a sterilization temperature and a sterilization cycle time in step 610. The method further includes introducing into the sterilization room a volume and concentration, or a measured unit dose, of a gas sufficient to act as a sterilant, such as, although not limited to, 100% ethylene oxide gas in step 620, and heating ethylene oxide to the set sterilization temperature in step 630. The method includes maintaining ethylene oxide at about the set sterilization temperature for the duration of the set sterilization cycle time in step 640 to facilitate diffusion of a sufficient amount of ethylene oxide into the interior of the containers. As ethylene oxide gas is maintained at about the set sterilization temperature, ethylene oxide molecules diffuse in and out of the containers, thereby creating a sterilizing atmosphere within each container in step 650. Maintaining ethylene oxide at about the set sterilization temperature also facilitates circulation of ethylene oxide throughout the sterilization room and within the interior of the containers to ensure a sufficient amount of ethylene oxide molecules contact substantially all surfaces of the musical instruments and/or accessories.

Upon expiration of the set sterilization cycle time, the method includes purging the sterilization room and containers by means of the exhaust ventilation system for a set purge cycle time in step 660 to exhaust residual ethylene oxide from the sterilization room and containers. The method further includes confirming after the expiration of the sterilization and purge cycles that one or more predetermined sterilization parameters have been achieved. In step 670, the containers are subsequently removed from the sterilization room, and in step 680 one or more biological and/or chemical sterilization monitoring devices is employed to confirm sterilization parameters. In one embodiment, the biological sterilization indicator known as SPOREVIEW® available from SPS Medical Supply Corp. of Rush, N.Y. is placed within the sterilization room and/or proximate to the container to indicate that the most challenging and hardy microbes have been eradicated. The container is then subjected to a degassing phase for a predetermined period of time in step 686 to reduce ethylene oxide in the container and musical instruments and/or accessories to a level safe for end-users. The musical instruments and/or accessories are then stored and supplied for end-use within the containers in step 690.

In a first aspect of the fifth embodiment, the method includes using one or more gas diffusion bags as containers to hold one or more musical instruments and/or accessories for sterilization in the sterilization room, as described above. The gas diffusion bag is similar to the gas diffusion bag described in the fourth embodiment of the method of the invention and constructed of a suitable material in part permeable to ethylene oxide, such as, although not limited to, 3 mil high density polyethylene. The high density polyethylene permits diffusion of ethylene oxide through the wall of the gas diffusion bag and into the interior of the gas diffusion bag to create a sterilizing atmosphere therein. Similar to the gas diffusion bag of the fourth embodiment, a band of TYVEK® is incorporated with and surrounds at least a portion of the perimeter of the gas diffusion bag. The TYVEK® band is preferably incorporated around the base of the gas diffusion bag and has a width of about 4 inches. The preferred sizes of the gas diffusion bag include, although are not limited to, 4×2 inches, for containing mouth pieces and small accessories, 16×29 inches, 33×46 inches and 28×52 inches.

Prior to sterilization, the gas diffusion bag is sealed by a suitable adhesive to form a substantially gas-impermeable, leak-proof and tamper-proof seal. In addition, as described above in the fourth embodiment, the gas diffusion bag further includes one-or more chemical monitoring devices incorporated with the gas diffusion bag to indicate that predetermined sterilization parameters have been achieved with respect to safety and health.

Having thus described at least one illustrative embodiment of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. A method of sterilizing an item, wherein the item is one of a musical instrument and a musical instrument accessory, using a gas diffusion process, comprising steps of:
   providing an open, sealable diffusion bag to contain the item;
   placing the item into an interior of the open diffusion bag;
   evacuating air from the diffusion bag;
   sealing the diffusion bag;
   positioning the diffusion bag in a chamber of a sterilizer having a ventilation system for removal of exhaust gas from the chamber;
   providing a sterilizing atmosphere in the interior of the diffusion bag by releasing into the diffusion bag ethylene oxide at a concentration sufficient to act as a sterilant;
   heating ethylene oxide to an appropriate temperature;
   maintaining the temperature of the ethylene oxide for a sufficient time to sterilize the item; and
   removing the diffusion bag from the sterilizer after the item is sterilized.

2. A method of sterilizing an item, wherein the item is one of a musical instrument and a musical instrument accessory using a gas diffusion process, comprising steps of:
   placing the item into an interior of a container;
   evacuating air from the container;
   sealing the container;
   positioning the container in a sterilization room having temperature control and a ventilation system for removal of exhaust gas from the room;
   creating a sterilizing atmosphere within the interior of the container by releasing into the sterilization room ethylene oxide in a concentration sufficient to act as a sterilant;
   heating ethylene oxide to an appropriate sterilization temperature;
   maintaining the sterilization temperature of the ethylene oxide for a sufficient time to sterilize the item; and
   removing the container from the sterilization room after the item is sterilized.

3. The method of claim 2, wherein the container is constructed of a material sufficiently permeable to ethylene oxide to facilitate diffusion of ethylene oxide from the atmosphere of the sterilization room into the interior of the container.

4. The method of claim 3, wherein the container includes a diffusion bag.

5. The method of claim 4, wherein the diffusion bag is constructed of a tear-resistant material.

6. The method of claim 1 or 4, wherein the diffusion bag is constructed of high density polyethylene.

7. The method of claim 6, wherein the diffusion bag further includes a band of material highly permeable to ethylene oxide.

8. The method of claim 7, wherein the band of material is incorporated with and surrounds at least a portion of the perimeter of the diffusion bag.

9. The method of claim 1 or 4, wherein sealing the diffusion bag includes forming a substantially leak-proof and tamper-proof seal.

10. The method of claim 1 or 4, wherein the concentration of ethylene oxide includes a unit dose measured in relation to a volume of the interior of the diffusion bag.

11. The method of claim 1 or 4, wherein the concentration of ethylene oxide is about 100%.

12. The method of claim 1 or 4, wherein the sterilization temperature at which ethylene oxide is maintained is about 45° C. to about 55° C.

13. The method of claim 1 or 4, wherein the time at which ethylene oxide is maintained at the sterilization temperature is about 4 hours to about 16 hours.

14. The method of claim 1 or 4, further comprising purging residual ethylene oxide from the diffusion bag for a sufficient time to substantially exhaust residual ethylene oxide from the diffusion bag.

15. The method of claim 14, wherein the sufficient time of purging is about 16 hours to about 24 hours.

16. The method of claim 1 or 4, further comprising confirming one or more predetermined sterilization parameters have been achieved.

17. The method of claim 16, wherein confirming one or more predetermined sterilization parameters includes employing a biological monitoring device.

18. The method of claim 16, wherein confirming one or more predetermined sterilization parameters includes employing a chemical monitoring device.

19. The method of claim 4, further comprising confirming one or more sterilization parameters have been achieved using a chemical monitoring device; wherein the chemical monitoring device is incorporated with the container.

20. The method of claim 1 or 4, further comprising degassing for a predetermined period of time to reduce ethylene oxide in the diffusion bag and the item contained therein to a predetermined level safe for end-use.

21. The method of claim 1 or 4, further comprising placing the item in a musical instrument carrying case prior to placing the item in the diffusion bag.

22. An item, wherein the item is one of a sterile musical instrument and an accessory related thereto which is sterilized by a gas sterilant diffusion process comprising
   placing the item into an interior of a gas permeable container;

evacuating air from the container;

sealing the container;

positioning the container in a sterilization chamber having temperature control and a ventilation system for removal of exhaust gas from the chamber;

creating a sterilizing atmosphere within the interior of the container by releasing into the chamber ethylene oxide at a concentration sufficient to act as a sterilant;

heating ethylene oxide to an appropriate sterilization temperature;

maintaining the sterilization temperature of the ethylene oxide for a sufficient time to sterilize the item; and removing the container from the chamber after the item is sterilized.

* * * * *